(12) United States Patent
Cho et al.

(10) Patent No.: US 10,390,789 B2
(45) Date of Patent: Aug. 27, 2019

(54) TWO-DIMENSIONAL X-RAY DETECTOR, CONE-BEAM CT APPARATUS AND METHOD USING REGION-OF-INTEREST

(71) Applicant: UNIVERSITY-INDUSTRY COOPERATION GROUP OF KYUNG HEE UNIVERSITY, Yongin-si, Gyeonggi-do (KR)

(72) Inventors: Min Hyoung Cho, Seongnam-si (KR); Soo Yeol Lee, Seongnam-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 250 days.

(21) Appl. No.: 15/537,017

(22) PCT Filed: Nov. 11, 2016

(86) PCT No.: PCT/KR2016/012986
§ 371 (c)(1),
(2) Date: Jun. 16, 2017

(87) PCT Pub. No.: WO2018/074650
PCT Pub. Date: Apr. 26, 2018

(65) Prior Publication Data
US 2018/0256128 A1 Sep. 13, 2018

(30) Foreign Application Priority Data
Oct. 17, 2016 (KR) .................. 10-2016-0134132

(51) Int. Cl.
*A61B 6/00* (2006.01)
*A61B 6/03* (2006.01)
(Continued)

(52) U.S. Cl.
CPC .............. *A61B 6/584* (2013.01); *A61B 6/032* (2013.01); *A61B 6/467* (2013.01); *A61B 6/469* (2013.01);
(Continued)

(58) Field of Classification Search
CPC ......... A61B 6/584; A61B 6/032; A61B 6/469; A61B 6/4085; A61B 6/4435; A61B 6/467; G06T 7/0012; G06T 7/11
See application file for complete search history.

(56) References Cited

U.S. PATENT DOCUMENTS

| 9,277,895 | B2 * | 3/2016 | Hara ..................... A61B 6/0407 |
| 9,283,404 | B2 * | 3/2016 | Raleigh .................... A61B 6/12 |

(Continued)

FOREIGN PATENT DOCUMENTS

| JP | 2007-097977 A | 4/2007 |
| JP | 2010-162154 A | 7/2010 |

(Continued)

OTHER PUBLICATIONS

International Search Report of PCT/KR2016/012986, dated Jun. 14, 2017. [PCT/ISA/210].

(Continued)

*Primary Examiner* — Kiho Kim
(74) *Attorney, Agent, or Firm* — Sughrue Mion, PLLC (57) ABSTRACT

Disclosed herein are a two-dimensional X-ray detector provided with a table of the position and size of a region-of-interest so as to change the position and size of the region-of-interest for each frame, and a cone-beam CT apparatus using the same and an operation method thereof. ROI projection data of a high resolution for a set ROI may be acquired, and the binning technique may be applied to non-ROI projection data created by the X-rays emitted onto (Continued)

a non-ROI region to acquire low-resolution data. Thereby, the amount of projection data may be reduced.

10 Claims, 6 Drawing Sheets

(51) Int. Cl.
*G06T 7/11* (2017.01)
*G06T 7/00* (2017.01)

(52) U.S. Cl.
CPC ............... *G06T 7/11* (2017.01); *A61B 6/4085* (2013.01); *A61B 6/4435* (2013.01); *G06T 7/0012* (2013.01)

(56) References Cited

U.S. PATENT DOCUMENTS 9,414,798 B2 * 8/2016 Feuerlein ............... A61B 6/032
2007/0230653 A1 10/2007 Okamoto et al.
2012/0307966 A1 12/2012 Roessl et al.
2015/0216498 A1 8/2015 Schulze et al.
2018/0333124 A1 * 11/2018 Kaneko ............... A61B 6/5235

FOREIGN PATENT DOCUMENTS

| KR | 10-1076319 B1 | 10/2011 |
| KR | 10-1323034 B1 | 11/2013 |
| KR | 10-2015-0041239 A | 4/2015 |

OTHER PUBLICATIONS

Communication dated May 18, 2018, issued by the Korean Patent Office in counterpart Korean Patent Application No. 10-2016-0134132.

* cited by examiner

| $s_0(0)$ |
|---|
| $t_0(0)$ |
| $w_R(0)$ |
| $h_R(0)$ |
| $s_0(1)$ |
| $t_0(1)$ |
| $w_R(1)$ |
| $h_R(1)$ |
| . . . . |
| . . . . |
| . . . . |
| $s_0(N-1)$ |
| $t_0(N-1)$ |
| $w_R(N-1)$ |
| $h_R(N-1)$ |

FIG. 8

TWO-DIMENSIONAL X-RAY DETECTOR, CONE-BEAM CT APPARATUS AND METHOD USING REGION-OF-INTEREST

CROSS-REFERENCE TO RELATED APPLICATION

This application claims priority to and the benefit of Korean Patent Application No. 10-2016-0134132, filed on Oct. 17, 2016, the disclosure of which is incorporated herein by reference in its entirety.

BACKGROUND OF THE INVENTION

Field of the Invention

The present invention relates to a two-dimensional X-ray detector provided with a table of the position and size of a region-of-interest (ROI) so as to change the position and size of the region-of-interest for each frame, and a cone-beam CT apparatus using the same and an operation method thereof.

Discussion of Related Art

A computed tomography (CT) system using X-rays utilizes the effect of attenuation of X-rays transmitted through an object. When X-rays are transmitted through an object, the intensity of the X-rays is attenuated by physical effects such as photoelectric absorption and Compton scattering. The degree of attenuation depends on the components and physical density of the object.

An X-ray tomogram may be considered as an X-ray attenuation coefficient image of components of an object. The X-ray attenuation coefficient generally increases as the density of a material and the atomic number of a component of the material increase.

For example, when a human body is subjected to imaging, the bone tissue and teeth of the human body have a higher X-ray attenuation coefficient than soft tissues (in general, the X-ray attenuation coefficient decreases as the X-ray photon energy increases).

Accordingly, in order to acquire a tomogram of an object, a set of projection images acquired by emitting an X-ray to the human body at various angles is required. Such a set of projection images is acquired by positioning an X-ray source and an X-ray detector on one gantry and rotating the gantry evenly.

Some tomography apparatuses obtain a set of projection images by fixing the X-ray source and the X-ray detector and rotating the object, but are based on the same principle as above.

The process of sequentially acquiring projection images at certain angles is called scanning. The scanning operation is generally performed using an X-ray CT scanner having single-element X-ray detectors arranged in an array.

The single-element X-ray detector is large and thick and has a high X-ray sensitivity, which is advantageous to get high signal-to-noise ratio (SNR) images. By arranging the single-element X-ray detectors on an arc, one-dimensional projection data can be acquired simultaneously at one scan angle and a cross-sectional image can be acquired by one revolution of the gantry.

In addition, when the single element X-ray detectors are arranged on a plurality of arcs, projection data of a plurality of sections can be acquired simultaneously, and images of a plurality of cross sections can be acquired by one revolution of the gantry.

CT having the structure described above is generally referred to as multi-ring CT. A multi-ring CT is generally used because it can shorten the scan time per section, compared to a single-ring CT.

A multi-ring CT provides a shorter imaging time than a single-ring X-ray CT, and it may have a helical scanning function, which enables 3D tomography.

However, a multi-ring CT requires that the gantry be rotated several times to perform helical scanning. In order to acquire a three-dimensional image by one revolution of the gantry, at least several hundred detector rings are required, which raises an economic issue.

To overcome this issue, a two-dimensional plane detector has been developed and commercialized. The two-dimensional plane detector has evolved to have more than several million pixels. Thereby, digital radiography has been developed and become common.

In addition, CT technology has also evolved according to development of the two-dimensional plane detector. Such a CT equipped with a two-dimensional plane detector is generally called a cone-beam CT. Representative examples of a cone-beam CT include a dental CT and a micro CT.

Since the cone-beam CT acquires projection images with a two-dimensional plane detector, a three-dimensional tomogram can be reconstructed by a single revolution of the gantry. Therefore, in order to increase the resolution of a CT image, the pixel size of the X-ray detector should be decreased and the total size of the detector should be sufficiently large enough to cover up a target object. Accordingly, the number of pixels of a high-resolution two-dimensional X-ray detector is usually larger than 2600×2600, i.e., 670 million.

In this case, the number of bits per pixel is generally 16, and one projection image has 100M bits or more. When this data is transmitted at a transfer rate of 1 Gbps, fewer than 10 images are theoretically collected per second.

As a transmission channel of a two-dimensional X-ray detector, GigE, Camera Link and USB are usually used. The physical transfer rate of a channel is about 1.0 to 5.0 Gbps. For a commercial detector having a resolution of 2600× 2600, about 7 images are collected per second on the GigE channel, and about 15 images are collected per second on the Camera Link. In most of CT imaging, more than about 450 images are captured per revolution. Accordingly, when 15 images are captured per second, an imaging time of 30 seconds or longer is required, and thus increase of the imaging speed is limited.

A conventional method for reducing the imaging time with a two-dimensional X-ray detector to a few seconds is to reduce the resolution of the detector by decreasing the number of pixels. The technique of reducing the number of pixels is called binning. With this technique, adjacent pixel data are combined to increase the pixel size as in the cases of 2×2, 4×4, 8×8, and 16×16, and thus the amount of data can be reduced as the resolution is reduced. Therefore, this technique may increase the number of projection images per second.

However, this conventional method basically relies on lowering the resolution and is not suitable for a high-resolution CT system. Therefore, there is a need for a method of performing high-speed imaging with a high resolution while overcoming the limitation in data transfer rate.

PRIOR ART DOCUMENT

Patent Literature

Korean Patent No. 10-1076319 (Oct. 18, 2011), "CONE-BEAM CT APPARATUS WITH DYNAMICALLY CONTROLLED COLLIMATOR"

Korean Patent No. 10-1323034 (Oct. 22, 2013), "CONE BEAM COMPUTERED TOMOGRAPHY APPARATUS

USING SINGLE ENERGY PHOTON SOURCE AND METHOD FOR ACQUIRING IMAGE USING THE SAME"

US Patent Application Publication No. 2015/0216498 (Aug. 6, 2015), "GEOMETRIC CHARACTERIZATION AND CALIBRATION OF A CONE-BEAM COMPUTER TOMOGRAHY APPARATUS"

SUMMARY OF THE INVENTION

It is an object of the present invention to provide a two-dimensional X-ray detector allowing dynamic setting of a region-of-interest (ROI) and performing high-speed imaging of a CT apparatus while overcoming the transfer rate limitations of projection data, a cone-beam CT apparatus including the same and an operation method thereof.

It is another object of the present invention to provide a two-dimensional X-ray detector allowing dynamic setting of an ROI by setting a position and size of the ROI for each frame based on an embedded ROI table and transmitting only projection data for the set ROI to reduce the amount of the projection data, a cone-beam CT apparatus including the same, and an operation method thereof.

It is another object of the present invention to provide a two-dimensional X-ray detector allowing dynamic setting of an ROI by acquiring ROI projection data of a high resolution for the set ROI and acquiring non-ROI projection data of a low resolution created with X-rays emitted onto a non-ROI region by applying a binning technique to reduce the amount of the projection data, a cone-beam CT apparatus including the same, and an operation method thereof.

In accordance with an aspect of the present invention, the above and other objects can be accomplished by the provision of a two-dimensional X-ray detector comprising: an ROI table having a position and size of a region-of-interest (ROI) settable for each frame; and an ROI controller configured to control the ROI based on the ROI table.

The ROI controller may acquire and transmit ROI projection data created by the X-rays emitted to the ROI.

The two-dimensional X-ray detector may further include a binning processor configured to reduce an amount of projection data by applying a binning technique to non-ROI projection data created by the X-rays emitted to a non-ROI region.

In accordance with another aspect of the present invention, there is provided a cone-beam computed tomography (CT) apparatus comprising: a two-dimensional X-ray detector configured to control a region-of-interest (ROI) based on an ROI table having a position and size of the ROI settable for each frame and to process projection data created by the X-rays emitted to the controlled ROI; and an image processor configured to reconstruct a tomogram by applying an image reconstruction algorithm to the projection data.

The two-dimensional X-ray detector may include an ROI table having the position and size of the ROI settable for each frame; and an ROI controller configured to control the ROI based on the ROI table.

The ROI controller may acquire and transmit ROI projection data created by the X-rays emitted to the ROI.

The two-dimensional X-ray detector may further include a binning processor configured to reduce an amount of the projection data by applying a binning technique to non-ROI projection data created by the X-rays emitted to a non-ROI region.

The two-dimensional X-ray detector may process the projection data by combining ROI data projected onto the ROI and non-ROI data projected onto a non-ROI region.

The image processor may apply an interpolation technique to the binning technique-applied non-ROI projection data to recover virtual high-resolution data to reconstruct the tomogram.

In accordance with yet another aspect of the present invention, there is provided a method for operating a two-dimensional X-ray detector allowing dynamic setting of a region-of-interest (ROI) and a cone-beam CT apparatus having the same, the method comprising: controlling the ROI based on an ROI table having a position and size of the ROI settable for each frame; processing projection data, the projection data comprising ROI projection data created by the X-rays emitted to the ROI and non-ROI projection data created by the X-rays emitted to a non-ROI region; and reconstructing a tomogram by applying an image reconstruction algorithm to the projection data.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The present invention will now be described more fully with reference to the accompanying drawings, in which exemplary embodiments of the invention are shown.

The terminology used in the present disclosure serves the purpose of describing particular embodiments only and is not intended to limit the disclosure. As used in the disclosure and the appended claims, the singular forms "a", "an" and "the" are intended to include the plural forms as well, unless context clearly indicates otherwise. It will be further understood that the terms "includes" and/or "including," when used in this specification, specify the presence of stated features, steps, operations, elements, and/or components, but do not preclude the presence or addition of one or more other features, steps, operations, elements, components, and/or groups thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the invention and the appended claims, the singular forms "a", "an" and "the" are intended to include the plural forms as well, unless context clearly indicates otherwise.

In addition, terms such as "first" and "second" are used herein merely to describe a variety of constituent elements, but the constituent elements are not limited by the terms. The terms are used only for the purpose of distinguishing one constituent element from another constituent element.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Meanwhile, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

Figure 1:
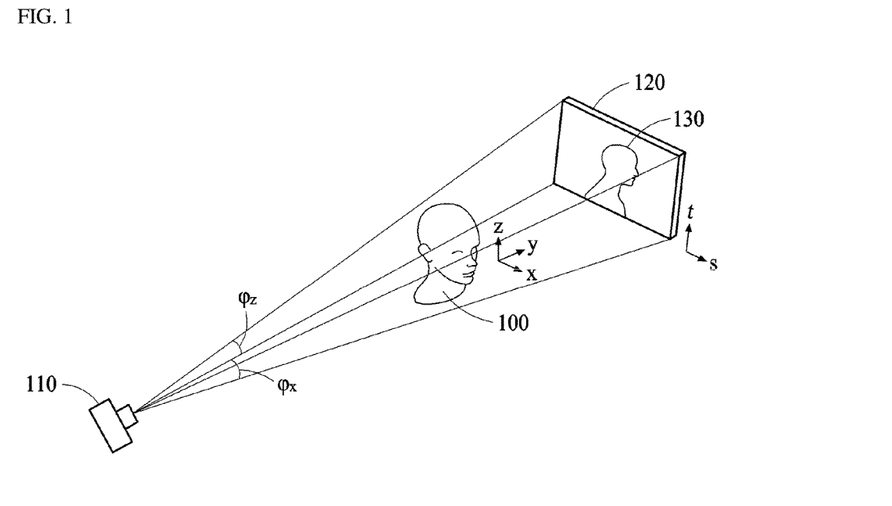
FIG. 1 illustrates an example of a cone-beam CT apparatus.

FIG. 1 illustrates an example of a cone-beam CT apparatus.

Referring to FIG. 1, the cone-beam CT apparatus includes an X-ray source 110 and a two-dimensional X-ray detector 120 arranged on opposite sides of an object 100, and acquires a projection image (or projection data) 130 at a given angle.

The X-rays emitted from the X-ray source 110 are spatially limited by a collimator installed at the outlet of the X-ray source 110 and may be generally limited based on the different sizes of the fields of view of the detector in the horizontal and vertical directions.

Here, limiting the size of the beam serves to reduce the X-ray dose emitted to the object 100 by limiting emission of the X-rays only to the field of view for imaging.

The X-ray source 110 and the two-dimensional X-ray detector 120 are capable of making rotational motion and translational motion. These elements are capable of making rotational motion with one degree of freedom and translational motion (linear motion) with one degree of freedom.

The center of rotation of the X-ray source 110 may be on the axis of translational motion of the X-ray source 110.

In an embodiment, the X-ray source 110 and the two-dimensional X-ray detector 120 may be configured to face each other and be rotated around the object 100 at a constant speed.

In another embodiment, the X-ray source 110 and the two-dimensional X-ray detector 120 may be fixed and the object 100 may be rotated to acquire a projection image 130. However, the projection image 130 projected by rotation of the X-ray source 110 and the two-dimensional X-ray detector 120 and the projection image 130 projected by rotation of the object 100 are based on the same principle.

Referring again to FIG. 1, $\varphi_x$ denotes a field of view in a horizontal direction, and $\varphi_z$ denotes a field of view in a vertical direction. In order to reconstruct a tomogram of the object 100, it is necessary to acquire projection images at various angles according to the fields of view in the horizontal direction and the vertical direction. Therefore, the cone-beam CT apparatus may move the X-ray source 110 and the two-dimensional X-ray detector 120 around the axis of rotation by a constant angle (unit scan angle) for each frame.

Figure 2:
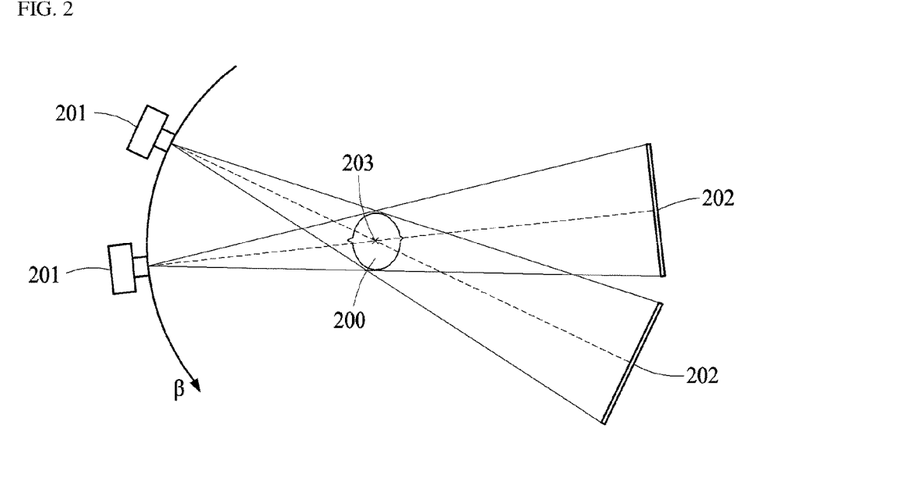
FIG. 2 illustrates an example of acquiring projection data through scanning in a cone-beam CT apparatus.

FIG. 2 illustrates an example of acquiring projection data through scanning in a cone-beam CT apparatus.

Referring to FIG. 2, the cone-beam CT apparatus performs scanning at a plurality of scan angles around an object 200 through an X-ray source 201 and a two-dimensional X-ray detector 202. Here, the axis of rotation 203 for scanning is located at the center of the object 200.

More specifically, the cone-beam CT apparatus may acquire projection data in a two-dimensional X-ray detector 202 created with X-rays emitted from the X-ray source 201 to the axis of rotation 203.

For example, the cone-beam CT apparatus may acquire a plurality of projection data at evenly-spaced scan angles separated by a unit scan angle, with respect to the axis of rotation 203.

Generally, as the unit scan angle decreases, namely, as the number of projection data increases, the spatial resolution of a tomogram is improved, but the imaging time increases. Thereby, the X-ray dose emitted to the patient increases.

On the other hand, if the number of projection data is excessively small, the spatial resolution of the tomogram may be degraded, and streak artifacts may appear, resulting in degradation of readability of the tomogram.

Therefore, the number of projection data in the cone-beam CT apparatus is generally set to 1,000 or less, but may be larger or smaller than 1,000 in some embodiments.

The cone-beam CT apparatus acquires a projection data set $\{p_i(s,t)\}$ according to scanning in each frame and may calculate a three-dimensional tomogram f(x, y, z) from the projection data set.

Here, in the projection data $p_i(s,t)$, s and t denote the coordinates on the horizontal axis and the vertical axis in the plane of the two-dimensional X-ray detector, and i denotes the number of rotations in unit scan angles (That is, when the unit scan angle is $\Delta\beta$, the scan angle according to the i-th rotation is $\beta=i\Delta\beta$, and i=0, 1, 2, . . . , N-1). In the three-dimensional tomogram f(x, y, z), (x, y, z) denotes three-dimensional spatial coordinates within the object 100 as shown in FIG. 1.

As the number of projection data sets increases, a higher-resolution tomogram may be acquired. An image reconstruction technique is used to acquire a tomogram from the projection data sets acquired from the cone-beam CT apparatus.

In the image reconstruction technique, spatial filtering is performed on the projection data and then back-projection is applied.

Generally, the cone-beam CT apparatus uses the Feldkamp algorithm as a filtered back-projection technique extended to three dimensions. The filtered back-projection image reconstruction technique is widely used because of its high spatial resolution and fast computation, but an iterative reconstruction algorithm may also be employed.

Referring again to FIG. 2, the cone-beam CT apparatus should use the two-dimensional X-ray detector 202 having a high resolution and a large number of pixels according to a small pixel size in order to acquire a high-resolution image.

However, the two-dimensional X-ray detector 202 of the conventional cone-beam CT apparatus has a low processing speed and a low data frame rate due to a huge amount of projection data for acquiring a high resolution image.

Accordingly, the two-dimensional X-ray detector according to an embodiment of the present invention sets a region-of-interest (ROI) and uses a method of processing data in a non-ROI region to reduce the amount of projection data.

For example, if only a small area of ⅓ W×⅓ H of the total size of the two-dimensional X-ray detector 202 having a width W and a height H is subjected to transmission, the amount of projection data is reduced to ⅑ times the total data amount, and the number of projection images per second is increased 9 fold. Accordingly, the imaging time may be reduced to ⅑ times the imaging time for the total area.

However, in this case, the projection data for the entire object 200 may not be acquired, and only the ROI projection data may be acquired as a three-dimensional image.

Accordingly, the two-dimensional X-ray detector according to an embodiment of the present invention applies the binning technique for lowering the resolution of the non-ROI projection data projected by the X-rays emitted to a non-ROI region.

The binning technique is a method of reducing the resolution and the amount of data by increasing the pixel size by combining the data of adjacent pixels in the projection data.

In general, the binning technique uses 2×2, 4×4, 8×8, and 16×16 binning modes. When 4×4 binning is used, the amount of data may be reduced to 1/16 times the original amount of data because 16 pixels are combined into one pixel.

Accordingly, the two-dimensional X-ray detector according to an embodiment of the present invention acquires high-resolution data only for the ROI of ⅓ W×⅓ H and applies 4×4 binning to the other region (outside the ROI) to acquire low-resolution data. Thereby, the amount of projection data may be reduced and the number of projection data (projection images) per second may be increased.

Figure 3:
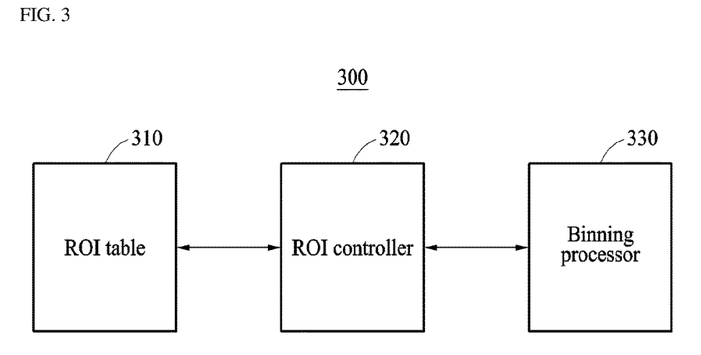
FIG. 3 is a block diagram illustrating configuration of a two-dimensional X-ray detector according to an embodiment of the present invention.

FIG. 3 is a block diagram illustrating configuration of a two-dimensional X-ray detector according to an embodiment of the present invention.

Referring to FIG. 3, a two-dimensional X-ray detector 300 according to an embodiment of the present invention controls the position and size of an ROI based on an ROI table for each frame.

To this end, the two-dimensional X-ray detector 300 according to an embodiment of the present invention includes an ROI table 310 and an ROI controller 320.

The ROI table 310 can set the position and size of a region-of-interest (ROI) for each frame.

Hereinafter, the ROI table will be described in detail with reference to FIG. 7.

Figure 7:
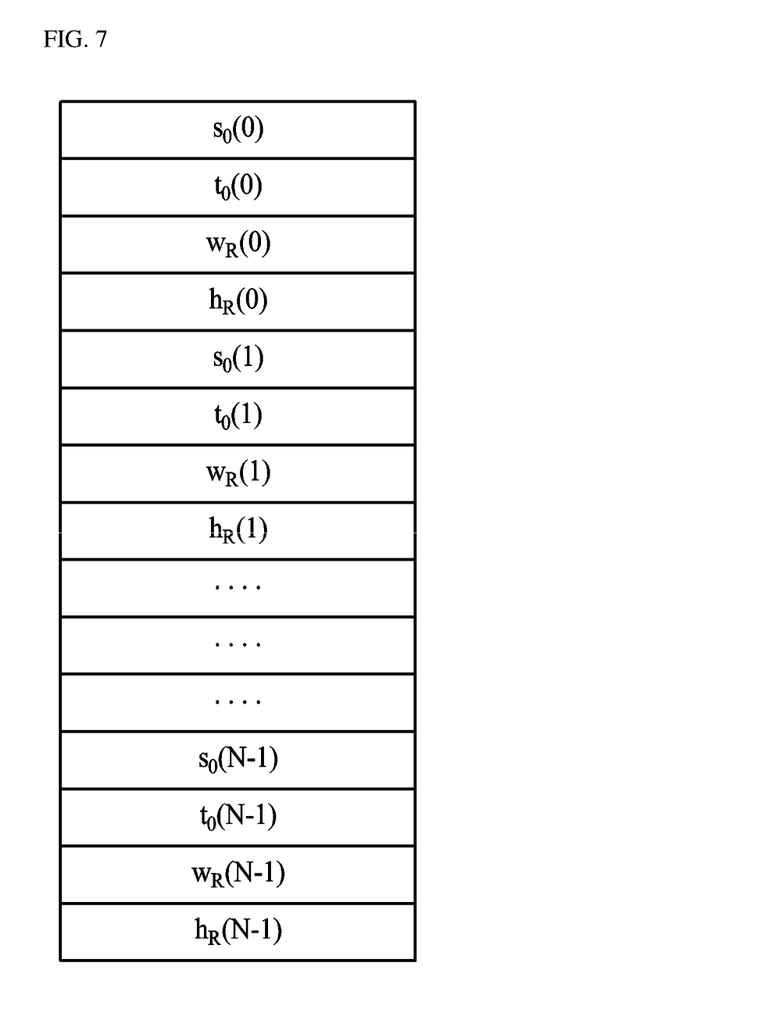
FIG. 7 illustrates an ROI table.

FIG. 7 illustrates an ROI table.

Referring to FIG. 7, the ROI table is set for N scan angles to acquire projection data, and includes movement information $(s_0, t_0, w_R, h_R)$ about the ROI preset by the N scan angles.

Here, $s_0$ and $t_0$ denote the coordinates of the start point of the ROI, $w_R$ denotes the width of the ROI, and $h_R$ denotes the height of the ROI.

The size including the movement coordinates, width, and height of the ROI included in the ROI table may be set differently according to the scan angle, the two-dimensional X-ray detector, and embodiments to which a cone-beam CT apparatus including the two-dimensional X-ray detector is applied.

For example, the two-dimensional X-ray detector according to an embodiment of the present invention may store movement information including the position and size of the ROI in the ROI table, and control the ROI by extracting the movement information about the ROI from the ROI table for each frame.

Referring back to FIG. 3, the ROI controller 320 of the two-dimensional X-ray detector 300 according to an embodiment of the present invention controls the ROI based on the ROI table 310.

More specifically, the ROI controller 320 may acquire and transmit only the ROI projection data created with X-rays emitted to the ROI.

In some embodiments, the ROI controller 320 may combine and transmit the ROI projection data projected by the X-rays emitted to the ROI and non-ROI projection data created with X-rays emitted to a non-ROI region.

In addition, the two-dimensional X-ray detector 300 according to an embodiment of the present invention may further include a binning processor 330 configured to apply the binning technique to the non-ROI projection data projected by the X-rays emitted to the non-ROI region to reduce the amount of projection data.

For example, the two-dimensional X-ray detector 300 according to an embodiment of the present invention may determine whether to transmit only the ROI projection data and whether to acquire non-ROI projection data to lower the resolution. The determination may be made based on a command from a user and may be performed according to a predetermined determination criterion of a program or software installed in the two-dimensional X-ray detector 300 according to an embodiment of the present invention.

The ROI controller 320 of the two-dimensional X-ray detector 300 according to an embodiment of the present invention may acquire only the ROI projection data projected onto the ROI excluding the non-ROI region, and transmit only the acquired ROI projection data, thereby reducing the amount of projection data and enhancing the data transfer rate.

In some embodiments, the ROI control unit 320 may acquire non-ROI projection data projected onto the non-ROI region and apply the binning technique of adding pixels to the non-ROI projection data in the binning processor 330 to acquire low-resolution projection data having a relatively low resolution.

Accordingly, the ROI controller 320 may acquire ROI projection data of a high resolution projected onto the ROI, acquire non-ROI projection data of a low resolution projected onto the non-ROI region, and combine the high-resolution projection data and the low-resolution projection data to reduce the amount of the projection data.

Figure 4:
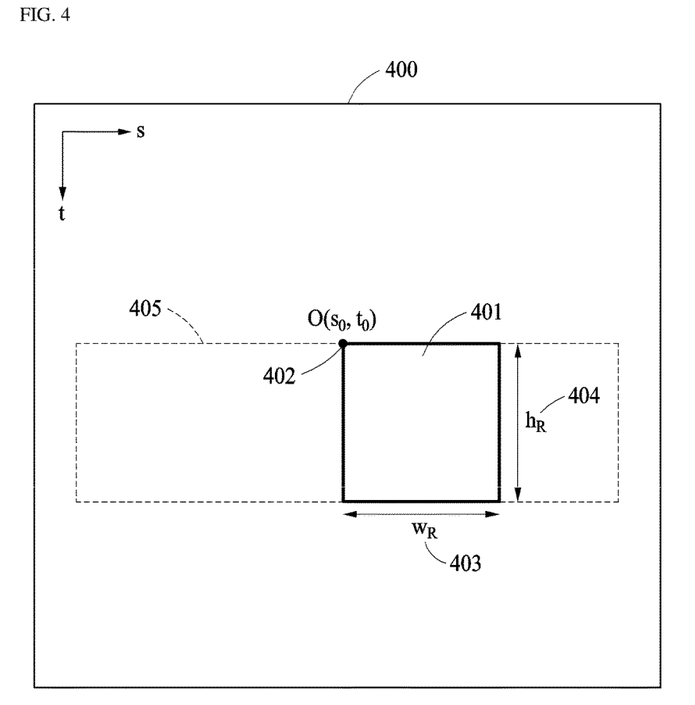
FIG. 4 illustrates an example of controlling the position and size of an ROI in a two-dimensional X-ray detector according to an embodiment of the present invention.

FIG. 4 illustrates an example of controlling the position and size of an ROI in a two-dimensional X-ray detector according to an embodiment of the present invention.

Referring to FIG. 4, a two-dimensional X-ray detector 400 according to an embodiment of the present invention controls the position and size of an ROI 401 based on an ROI table.

For example, the two-dimensional X-ray detector 400 according to an embodiment of the present invention may move the ROI 401 in the horizontal direction 405.

In some embodiments, when the coordinates 402 of the ROI 401 are O(s0, t0), the width 403 is $w_R$, and the height 404 is $h_R$, the two-dimensional X-ray detector 400 may control the position and size of the ROI 401 based on the movement information of the ROI table including information about the coordinates 402, width 403 and height 404 of the ROI 401.

Accordingly, the two-dimensional X-ray detector 400 according to an embodiment of the present invention may use the ROI information including the movement information about the ROI 401 preset by N scan angles to more accurately control the size and movement of the ROI 401 for each frame.

Figure 5:
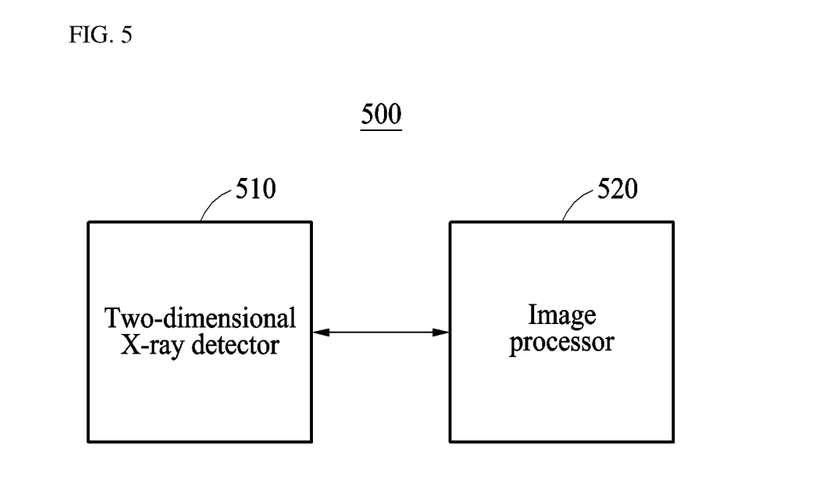
FIG. 5 is a block diagram illustrating configuration of a cone-beam CT apparatus including a two-dimensional X-ray detector allowing dynamic setting of an ROI according to an embodiment of the present invention.

FIG. 5 is a block diagram illustrating configuration of a cone-beam CT apparatus including a two-dimensional X-ray detector allowing dynamic setting of an ROI according to an embodiment of the present invention.

Referring to FIG. 5, a cone-beam CT apparatus 500 including a two-dimensional X-ray detector allowing dynamic setting of an ROI, according to an embodiment of the present invention, controls the position and size of an ROI based on an ROI table, and reconstructs a tomogram by applying an image reconstruction algorithm to the projection data received from the two-dimensional X-ray detector configured to process the projection data created by the X-rays emitted to the ROI.

To this end, the cone-beam CT apparatus 500 includes a two-dimensional X-ray detector 510 and an image processor 520.

The two-dimensional X-ray detector 510 controls the ROI based on the ROI table in which the position and size of the ROI can be set for each frame, and processes the projection data created with X-rays emitted to the controlled ROI.

For example, the two-dimensional X-ray detector 510 may control the position and size of the ROI in sequential order of movement information based on the ROI table.

More specifically, the two-dimensional X-ray detector 510 may include an ROI table (not shown) including the position and size of the ROI settable for each frame, an ROI controller configured to control the ROI based on the ROI table and a binning processor (not shown) configured to reduce the amount of projection data by applying the binning technique to non-ROI projection data created with X-rays emitted to a non-ROI region.

According to an embodiment, the two-dimensional X-ray detector 510 may acquire only the ROI projection data projected onto the ROI except for the non-ROI region, and may transmit only the acquired ROI projection data to reduce the amount of projection data to improve the transfer rate.

According to another embodiment, the two-dimensional X-ray detector 510 may acquire non-ROI projection data projected onto a non-ROI region, and acquire projection data having a resolution lower than the resolution of the ROI projection data by applying the binning technique of adding pixels to the acquired non-ROI projection data.

Accordingly, the two-dimensional X-ray detector 510 may acquire and combine the ROI projection data of a high resolution projected onto the ROI and the non-ROI projection data of a low resolution projected onto the non-ROI region, thereby reducing the amount of projection data to be transmitted.

The image processor 520 reconstructs a tomogram by applying an image reconstruction algorithm to the processed projection data.

The projection data may include only the ROI projection data, or may include both the ROI projection data and the non-ROI projection data obtained by applying the binning technique. The projection data may cover all the projection images projected onto the two-dimensional X-ray detector 510.

For example, the image processor 520 may reconstruct a tomogram by applying the image reconstruction algorithm to at least one of the ROI projection data and the non-ROI projection data.

The image processor 520 may interpolate the non-ROI projection data obtained by applying the binning technique in order to restore virtual high-resolution data to reconstruct the tomogram.

The image reconstruction algorithm may be performing spatial filtering on the projection data and then performing back-projection. In some embodiments, a three-dimensional extended back-projection technique, called the Feldkamp algorithm, may be used.

As an image reconstruction algorithm, an iterative reconstruction technique such as SART (Simultaneous Algebraic Reconstruction Technique) may be applied.

According to another embodiment, the cone-beam CT apparatus 500 may further include a detector controller (not shown).

For example, the detector controller may control the two-dimensional X-ray detector 510 based on user input.

In addition, the detector controller may control the operation of the two-dimensional X-ray detector 510 by generating a control command according to determination of whether to exclude the non-ROI region and whether to lower the resolution by acquiring non-ROI projection data for the non-ROI region.

Here, the control command may be at least one of addition, deletion, and modification of movement information included in the ROI table, or may be a control command according to at least one of on/off and motion of the two-dimensional X-ray detector 510.

According to another embodiment, the cone-beam CT apparatus 500 may further include a communication unit to transmit at least one of a reduced amount of projection data (projection data including only the ROI projection data, or projection data including both ROI projection data of a high-resolution and non-ROI projection data of a low-resolution) and a reconstructed tomogram to the outside.

Figure 6:
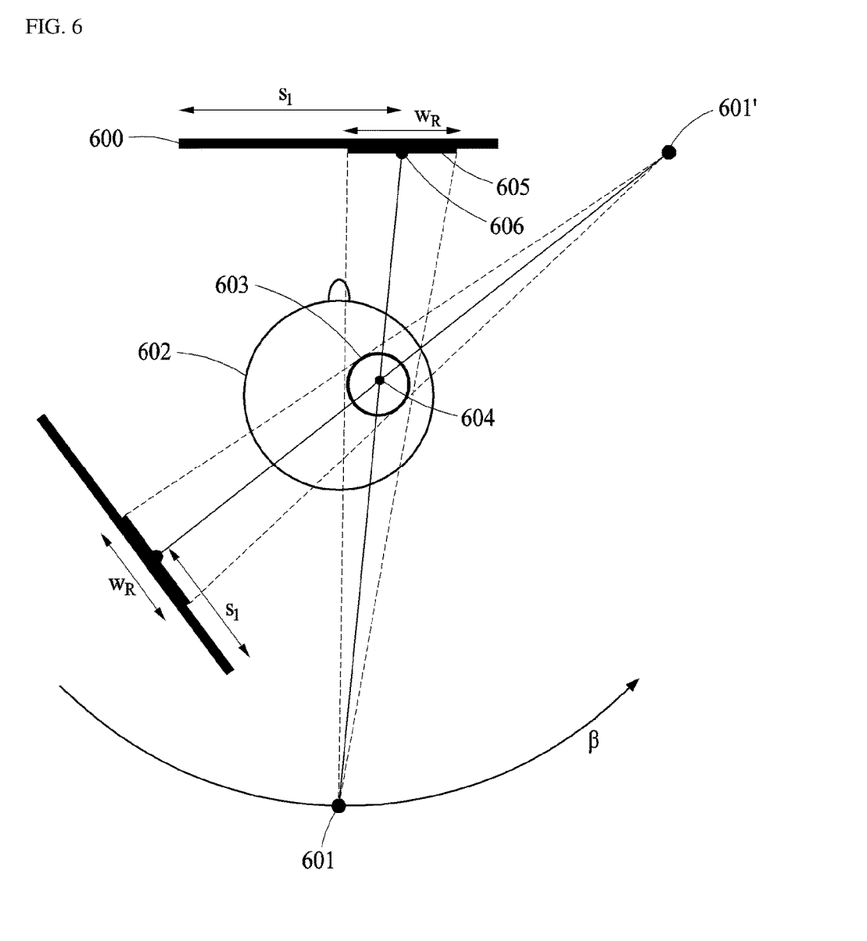
FIG. 6 illustrates an example of acquiring projection data using a cone-beam CT apparatus including a two-dimensional X-ray detector allowing dynamic setting of an ROI according to an embodiment of the present invention.

FIG. 6 illustrates an example of acquiring projection data using a cone-beam CT apparatus including a two-dimensional X-ray detector allowing dynamic setting of an ROI according to an embodiment of the present invention.

Referring to FIG. 6, a cone-beam CT apparatus including a two-dimensional X-ray detector allowing dynamic setting of an ROI according to an embodiment of the present invention acquires projection data (projection images) of an object 602 from an X-ray source 601 and a two-dimensional X-ray detector 600.

For example, the area of a circle having a radius r from the center point 604 inside the object is set to an ROI 603, and the cone-beam CT apparatus including the two-dimensional X-ray detector allowing dynamic setting of an ROI according to an embodiment of the present invention acquires projection data created on the two-dimensional X-ray detector 600 by X-rays emitted onto the ROI 603 of the object.

Here, the X-ray emitted to the center point 604 inside the object points to the center point 606 of the ROI in the two-dimensional X-ray detector 600.

Referring to FIG. 6, in a cone-beam CT apparatus including a two-dimensional X-ray detector allowing dynamic setting of a region-of-interest according to an embodiment of the present invention, when a horizontal coordinate of the center point 606 of the ROI is $s_1$, and the width of the ROI 605 is $w_R$, $s_1$ and $w_R$ are changed each time by the scan angle $\beta$ according to the unit scan angle.

However, the coordinates and width varying by the scan angle may be obtained based on the correct values of $s_1$, $w_R$, and the start coordinates ($s_0$, $t_0$) of the ROI 605 according to a simple geometric solution. In an embodiment, $s_1$ may be a sine function of the scan angle.

For example, when the width of the scan angle does not greatly deviate from a set reference, it is possible to approximate $s_0 = s_1 - w_R/2$, taking $w_R$ as a constant.

Therefore, in the cone-beam CT apparatus including a two-dimensional X-ray detector allowing dynamic setting of the ROI according to an embodiment of the present invention, the two-dimensional X-ray detector 600 may control the position and size of the ROI 605 for each frame to acquire projection data of a high resolution according to the ROI 603 of the object.

Figure 8:
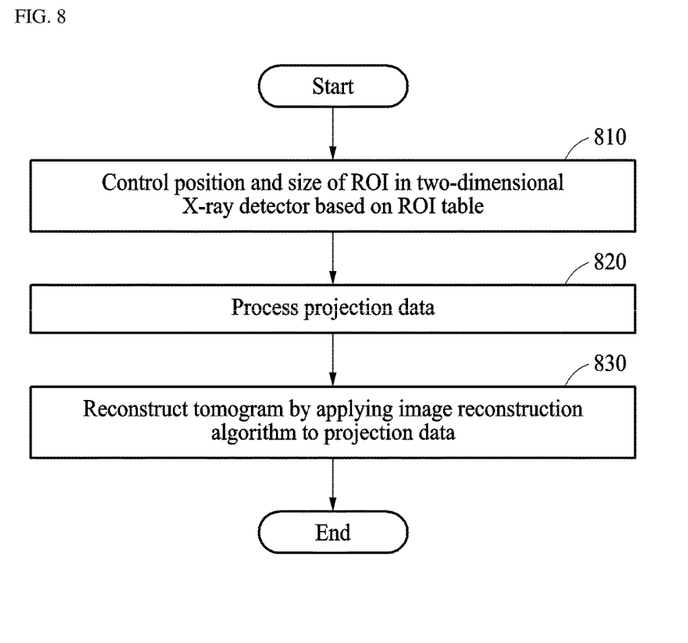
FIG. 8 is a flowchart illustrating a method of operating a two-dimensional X-ray detector allowing dynamic setting of an ROI and a cone-beam CT apparatus including the same according to an embodiment of the present invention.

FIG. 8 is a flowchart illustrating a method of operating a two-dimensional X-ray detector allowing dynamic setting of an ROI and a cone-beam CT apparatus including the same according to an embodiment of the present invention.

Referring to FIG. 8, in step 810, the position and size of the ROI in the two-dimensional X-ray detector are controlled based on the ROI table in which the position and size of the ROI can be set for each frame.

Step 810 may be to sequentially control the position and size of the ROI in the two-dimensional X-ray detector based on the ROI table.

In step 820, the projection data including the ROI projection data created with X-rays emitted to the ROI and the non-ROI projection data created with X-rays emitted to a non-ROI region are processed.

According to an embodiment, step 820 may include acquiring only the ROI projection data projected onto the ROI, except the non-ROI region.

According to another embodiment, step 820 may include acquiring non-ROI projection data created on a two-dimensional X-ray detector by X-rays emitted to a non-ROI region and applying a binning technique of adding pixels to the acquired non-ROI projection data.

In step 830, an image reconstruction algorithm is applied to the projection data to reconstruct a tomogram.

Step 830 may include reconstructing a tomogram by applying the image reconstruction algorithm to at least one of the ROI projection data and the non-ROI projection data.

According to embodiments of the present invention, the limitation of the data transfer rate of projection data may be overcome and high-speed imaging may be performed by a CT apparatus.

According to embodiments of the present invention, the position and size of an ROI may be set for each frame based on the embedded ROI table, and the amount of the projection data may be reduced by transmitting only the projection data for the set ROI.

According to embodiments of the present invention, the ROI projection data of a high resolution for the set ROI may be acquired, and the binning technique may be applied to the non-ROI projection data created by the X-rays emitted onto a non-ROI region to acquire low-resolution data. Thereby, the amount of projection data may be reduced.

Embodiments of the present invention can include a computer readable medium including program commands for executing operations implemented through various computers. The computer readable medium can store program commands, data files, data structures or combinations thereof. The program commands recorded in the medium may be specially designed and configured for the present invention or be known to those skilled in the field of computer software. Examples of a computer readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands. Examples of the program commands include a machine language code created by a compiler and a high-level language code executable by a computer using an interpreter and the like. The hardware devices may be configured to operate as one or more software modules to perform operations in the embodiments, and vice versa.

Although exemplary embodiments of the present invention have been disclosed for illustrative purposes, those skilled in the art will appreciate that various modifications, additions and substitutions are possible, without departing from the scope and spirit of the invention as disclosed in the accompanying claims. For example, proper result may be achieved even if the techniques described above are implemented in an order different from that for the disclosed method, and/or disclosed constituents such as a system, structure, device and circuit are coupled to or combined with each other in a form different from that for the disclosed method or replaced by other constituents or equivalents.

It should be understood, however, that there is no intent to limit the invention to the embodiments disclosed, rather, the invention is to cover all modifications, equivalents, and alternatives falling within the spirit and scope of the invention as defined by the claims.

DESCRIPTION OF SYMBOLS 100, 200, 602: Object
110, 201, 601: X-ray source
120, 202, 600, 400: Two-dimensional X-ray detector
130: Projection image (projection data)
203: Axis of rotation
603: ROI of object
604: Center point 604 inside object
605, 401: ROI
606: Center point of ROI
402: Coordinates of ROI
403: Width of ROI
404: Height of ROI
405: Horizontal direction

What is claimed is:

1. A two-dimensional X-ray detector comprising:
an ROI table having a position and size of a region-of-interest (ROI) settable for each frame; and
an ROI controller configured to control the ROI based on the ROI table.

2. The two-dimensional X-ray detector of claim 1, wherein the ROI controller acquires and transmits ROI projection data created with X-rays emitted to the ROI.

3. The two-dimensional X-ray detector of claim 1, further comprising:

a binning processor configured to reduce an amount of projection data by applying a binning technique to non-ROI projection data created by the X-rays emitted to a non-ROI region.

4. A cone-beam computed tomography (CT) apparatus comprising:

a two-dimensional X-ray detector configured to control a region-of-interest (ROI) based on an ROI table having a position and size of the ROI settable for each frame and to process projection data created by the X-rays emitted to the controlled ROI; and an image processor configured to reconstruct a tomogram by applying an image reconstruction algorithm to the projection data.

5. The cone-beam CT apparatus of claim 4, wherein the two-dimensional X-ray detector comprises:

the ROI table having the position and size of the ROI settable for each frame; and an ROI controller configured to control the ROI based on the ROI table.

6. The cone-beam CT apparatus of claim 5, wherein the ROI controller acquires and transmits ROI projection data created by the X-rays emitted to the ROI.

7. The cone-beam CT apparatus of claim 5, wherein the two-dimensional X-ray detector further comprises:

a binning processor configured to reduce an amount of the projection data by applying a binning technique to non-ROI projection data created by the X-rays emitted to a non-ROI region.

8. The cone-beam CT apparatus of claim 7, wherein the image processor applies an interpolation technique to the binning technique-applied non-ROI projection data to recover virtual high-resolution data to reconstruct the tomogram.

9. The cone-beam CT apparatus of claim 4, wherein the two-dimensional X-ray detector processes the projection data by combining ROI data projected onto the ROI and non-ROI data projected onto a non-ROI region.

10. A method for operating a two-dimensional X-ray detector allowing dynamic setting of a region-of-interest (ROI) and a cone-beam CT apparatus having the same, the method comprising:

controlling the ROI based on an ROI table having a position and size of the ROI settable for each frame;

processing projection data, the projection data comprising ROI projection data created by the X-rays emitted to the ROI and non-ROI projection data created by the X-rays emitted to a non-ROI region; and reconstructing a tomogram by applying an image reconstruction algorithm to the projection data.

* * * * *